United States Patent [19]

Näslund

[11] Patent Number: 4,605,011
[45] Date of Patent: Aug. 12, 1986

[54] CELL SAMPLING APPARATUS

[76] Inventor: Jan I. Näslund, Vassvägen 21, S-141 39 Huddinge, Sweden

[21] Appl. No.: 588,954

[22] Filed: Mar. 13, 1984

[30] Foreign Application Priority Data

Mar. 23, 1983 [SE] Sweden ................ 8301598

[51] Int. Cl.⁴ ............................................. A61B 10/00
[52] U.S. Cl. ..................................... 128/752; 128/755
[58] Field of Search ............... 128/749, 755, 752–754, 128/763; 604/35, 117, 156

[56] References Cited

U.S. PATENT DOCUMENTS

| | | | |
|---|---|---|---|
| 2,705,949 | 4/1955 | Silverman | 128/754 |
| 2,818,852 | 1/1958 | Kugler | 128/755 |
| 3,692,020 | 9/1972 | Schied | 128/755 |
| 4,314,560 | 2/1982 | Helfgott et al. | 604/35 X |
| 4,461,305 | 7/1984 | Cibley | 128/754 |

FOREIGN PATENT DOCUMENTS

| | | | |
|---|---|---|---|
| 139087 | 12/1979 | German Democratic Rep. | 128/755 |
| 683726 | 9/1979 | U.S.S.R. | 128/755 |

*Primary Examiner*—Edward M. Coven

[57] ABSTRACT

Apparatus for taking samples of cells of small tumors with the aid of fine-needle puncturing techniques. The apparatus includes a hand-grip (1) having removably connected thereto a syringe provided with a thin cannula (2). The cannula (2) is connected, via a coupling (18), to a motor (12,13,15,16) which can be energized for driving the cannula (2) in an oscillating, reciprocatory movement. The cannula (2) is connected to a container (4) having arranged for movement therein a suction plunger (5), which is arranged to create a vacuum in the cannula (2), for drawing a cell sample thereinto.

11 Claims, 8 Drawing Figures

CELL SAMPLING APPARATUS

The present invention relates to apparatus for taking samples of cells from small tumours with the aid of fine-needle puncturing techniques, said apparatus comprising a hand-grip to which there is removably fitted a syringe having a fine cannula.

At the present time, fine-needle techniques are widely used to take cells from tumours in order to establish whether the tumours are benign or malignant. The accuracy with which the diagnosis can be made is greatly dependent upon the technique used. Thus, the person who is used to taking puncture samples will obtain a representative sample more often than the person who is unacquainted with puncturing techniques.

Cytological diagnosis with the aid of fine-needle puncturing started in the 1950's, when it was shown that individual cells released from tumours by means of this technique could be recognized and classified. This meant that it was no longer necessary to cut-out suspicious swellings from different parts of the body, in order to carry out an examination. The samples are taken with the aid of a thin needle, a so-called cannula, which is connected to a syringe in which a vacuum is created during the sampling process. To this end, the syringe is placed in a specially designed sampling hand-grip, it being possible to create the suction effect through the hand-grip. When the needle has been inserted into the tumour, a vacuum is created in the syringe by withdrawing the plunger located therewithin. Subsequent hereto, the person taking the sample attempts to move the point of the needle backwards and forwards in the tumour as quickly as possible, while maintaining the position of the puncture in the syringe constant, with the one and the same hand. Cells are released by the point of the needle and drawn thereinto. Subsequent to taking the sample, the cells are ejected onto a glass plate, where they are fixed and coloured and then determined cytologically.

In recent years, it has been possible to detect smaller and smaller tumours, through the increased awareness of patients and doctors, and, above all, through the technical development of mammography, datathermography, and ultrasonic examinations. Unfortunately, tumours smaller than 5 mm in size are unable to accompany the movements of the cannula during a sampling process, due to the position of such tumours in loose fatty tissue, thereby preventing the needle, or trocar, of the cannula from moving in the tumour. In addition hereto, the person making the puncture is unable to ascertain whether or not the cannula has been actually inserted to the correct position, since it is relatively easy to place the cannula point in surrounding tissue. Moreover, the oscillatory movements of the hand are not sufficiently rapid and accurate with respect to scope, even in the case of one who is really expert in the matter.

An object of the present invention is to remove the aforementioned deficiencies of known sampling apparatus which use a syringe and cannula, and to provide an apparatus with which one who is not skilled in taking samples using puncturing techniques can obtain substantially the same good results as one who is skilled in this art.

The apparatus according to the invention is characterized in that the cannula is connected to a motor, via a coupling, which can be energized to drive the cannula in an oscillating reciprocating piston-like movement, and in that the cannula is connected to a container in which a suction piston can be moved to produce a vacuum in the cannula, for drawing cell samples thereinto.

The apparatus according to the invention enables the position of the point of the cannula to be located precisely at the moment of taking the sample. Thus, it is possible in stereotactic breast X-rays to localize a tumour 2 mm in size, and to puncture the tumour with the cannula correctly positioned under view. The cannula point can then be oscillated at a given frequency and at a given length of stroke. When using, for example, a frequency of 50 strokes per second, the small tumour is unable to accompany the movement of the cannula. Practical tests have shown that excellent representative results can also be obtained with tumours of such small size.

Small tumours have been investigated in vitro by means of the new apparatus, and results have exceeded all expectations. With the aid of said apparatus, a totally untrained laboratory assistant has been successful in obtaining representative materia for specialized analysis from tumours of only some millimeters in size, where a highly trained cytologist and puncture expert has failed with manual puncturing techniques.

The invention will now be described in more detail with reference to the accompanying drawings, in which two embodiments of an apparatus according to the invention are illustrated.

Figure 1:
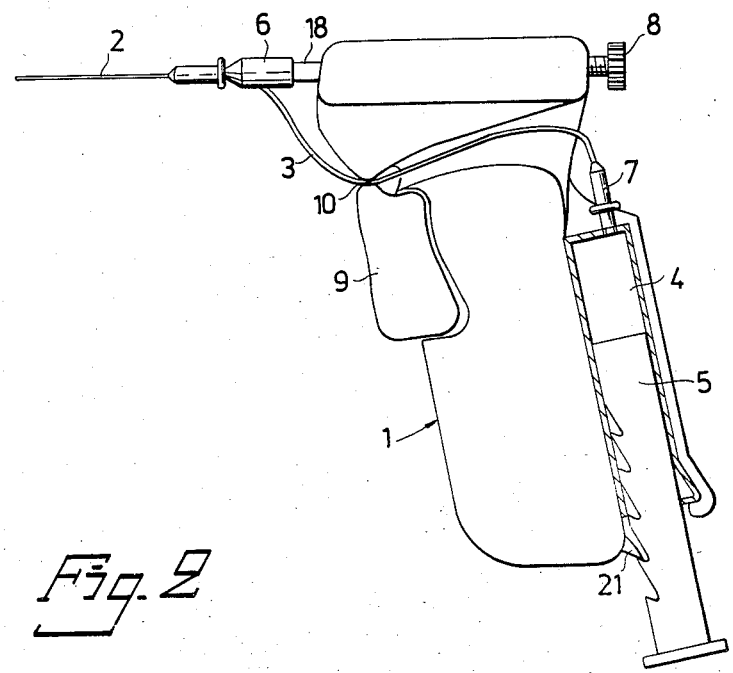
FIG. 1 is a side view of a first embodiment of the apparatus, in which a part of the casing facing the viewer has been removed.
Figure 2:
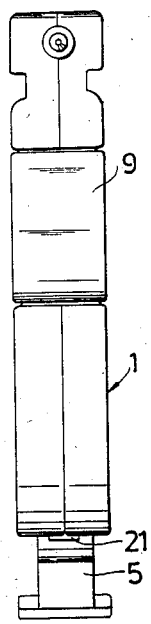
FIG. 2 is a front view of the apparatus illustrated in FIG. 1.
Figure 3:
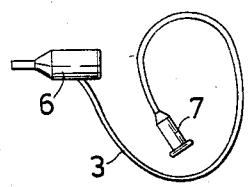
FIG. 3 illustrates a connecting hose between cannula and container in the apparatus illustrated in FIG. 1.
Figure 4:
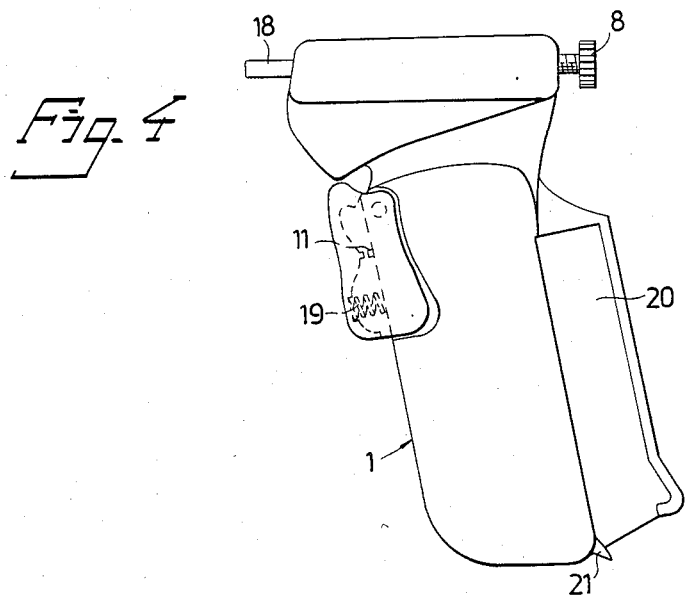
FIG. 4 is a side view of the apparatus illustrated in FIG. 1, a number of components having been removed from the casing.
Figure 5:
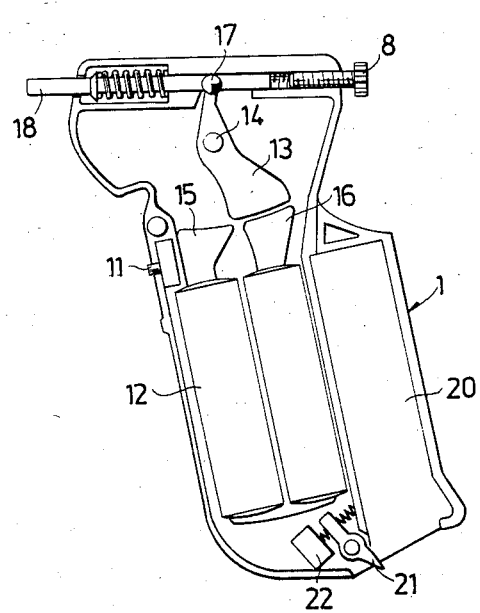
FIG. 5 is a further side view of the apparatus illustrated in FIG. 1, in which the whole of the side of the casing facing the viewer has been removed, together with some of the members within the casing.

The apparatus illustrated in FIG. 1 comprises a handle or hand-grip 1, which simultaneously forms a casing or housing for the apparatus components. Connected to the front of the apparatus is a function needle or cannula 2, the channel of which is connected, via a hose 3, with a container 4 having a suction-plunger 5 arranged for movement therein. The hose 3 together with cannula connection 6 and container connection 7 may either be designed for one-time use only or for re-use, depending upon the extent to which the hose is contaminated when taking the sample. The length of stroke of the cannula 2 can be adjusted by means of an adjusting screw 8. The apparatus is provided with a trigger 9 having a tongue 10 which squeezes the hose, so that the effect of the vacuum does not reach the cannula 2. When the trigger 9 is pressed, the vacuum reaches the cannula 2, whereupon a microswitch 11 closes the electric circuit to the winding of an electromagnet 12, whereupon a pole shoe 13, which can be swung about a point 14, oscillates backwards and forwards between poles 15 and 16 of the magnet. One end 17 of the pole shoe 13 is journalled in a recess of the cannula-holder rod 18, which causes the rod, together with the cannula, to execute a reciprocating movement when energizing the circuit of magnet 12. When the trigger 9 is released, the trigger is returned to its original position by means of a thrust spring 19. This de-energizes the circuit of magnet 12, causing the magnet-motor to stop, and simultaneously closes the vacuum prevailing in the syringe from the cannula, thereby enabling the cannula to be withdrawn without all the content thereof being drawn into the syringe. The container 4 and the plunger 5 are replaceably arranged in a chamber 20. The position of the plunger 5 in the container is regulated by means of the stop member 21, which engages a tooth part of the plunger. A vacuum is created in the container 4, when the plunger 5 is drawn downwardly. If the plunger is drawn upwardly, by the force of the vacuum created, a microswitch 22 is energized when a pre-set shoulder forces up the flip-over means 21. When the plunger 5 is drawn down, a certain underpressure is created in the syringe, which provides a given tensile force. The plunger is then locked in position, with the aid of the flip-over means 21. The switch 22 is connected in series with the contact breaker 11 of the trigger 9.

Figure 6:
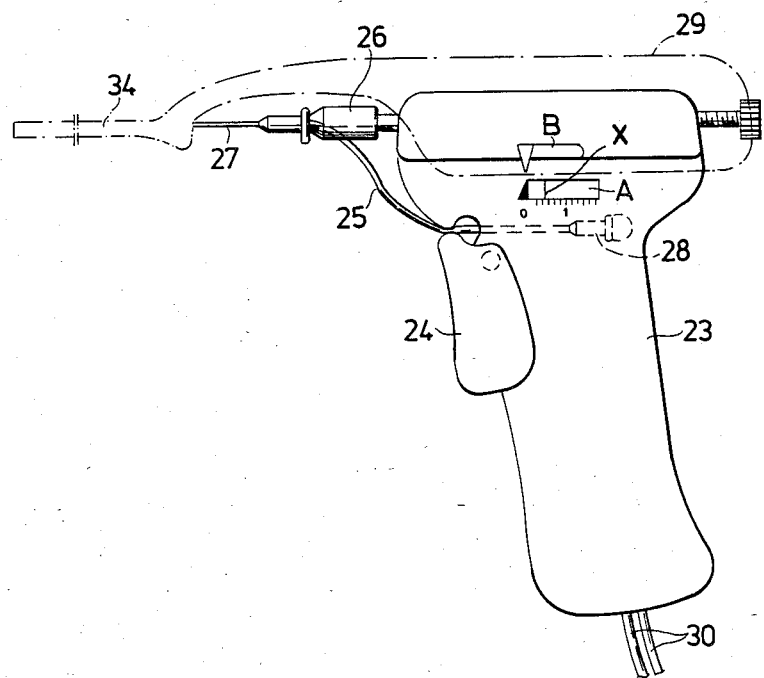
FIG. 6 is a side view of a second embodiment of the apparatus according to the invention, which is provided with control means for determining the functioning depth, said means being shown in broken lines.
Figure 7:
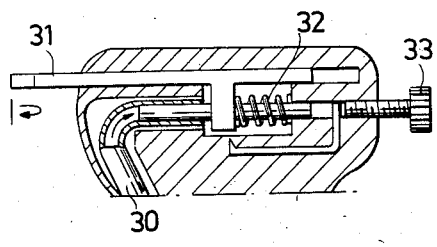
FIG. 7 is a side view of an upper part of the apparatus illustrated in FIG. 6, illustrating certain components within the apparatus.
Figure 8:
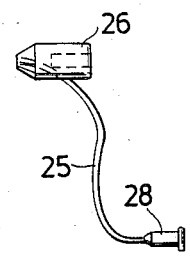
FIG. 8 is a view of the connecting hose between cannula and container in the apparatus illustrated in FIG. 6. In the drawings, like components are identified by like reference numerals.

The construction of the apparatus illustrated in FIGS. 6, 7 and 8 is substantially similar to that aforedescribed, said apparatus comprising a casing 23, a trigger 24, a hose 25 with connection 26 to cannula 27, and a connection 28 to a container not shown. This apparatus is also provided with a removable control means 29, which encloses the upper part of the apparatus on both sides thereof, and which determines the functional depth of the cannula 27. This apparatus is driven pneumatically or hydraulically, as opposed to the electric drive of the apparatus illustrated in FIG. 1. The apparatus includes lines 30, for applying pneumatic or hydraulic pressure. The cannula, together with its holder 31, is moved rearwardly to a limit position against the action of spring 32 which is compressed when pressure is applied by way of a pneumatic or hydraulic cylinder, not shown. On termination of supply of pneumatic or hydraulic pressure, spring 32 urges the cannula forwardly for insertion into the tissue. The length of stroke of the cannula is dependent on the length of stroke on the adjusted position of knob 33 and may be visually determined by means of a runner B on the control means 29 and a movable slide indicator X which moves along scale A provided on the hand grip below runner B. The length of the stroke and thus the extent of penetration of the cannula into the tissue can be readily determined if the position of the pointer on runner B is set at zero on the scale A when the setting of the knob 33 is such that the point of the cannula reaches the end of runner 34. The indicator X is operatively connected to the cannula holder 31 for movement therewith. It will thus be appreciated that the operator can readily determine the extent of penetration of the cannula into the tissue and thus the length of the stroke thereof by observing the position of the marking X on the scale A. The frequency and length of stroke of the apparatus can be regulated by means of suitable constriction in the lines 30. This enables regulations to be made over a wide area, and also enables accurate simulation of the movements of the hand of a well-trained puncture technician. The sampling operation is not appreciably affected by the resistance offered by tissue of varying kinds and sizes.

In the aforegoing there has been described two embodiments of an apparatus according to the invention, where the motor driving the cannula 2 comprises an electromagnet or a pneumatic or hydraulic motor.

An important characteristic is that when the cannula is inserted it adopts its terminal position, and hence there is no risk of the cannula being pushed too far forwards at the beginning of a sampling operation, and therewith damage important organs, such as large blood vessels, or cause great pain, such as when striking a rib for example.

Not all of the possible components of the apparatus have been described and the apparatus may be provided with various kinds of additional members and elements necessary for its function.

What I claim is:

1. Apparatus for taking samples of cells from small tumours by means of fine-needle puncture techniques, said apparatus comprising a hand-grip having a trigger for operating the apparatus by activating the trigger, said hand-grip having detachably connected thereto a syringe provided with a cannula connected via a coupling to a motor energized on activation of said trigger to drive the cannula in an oscillating reciprocatory movement, said cannula being connected to a container forming part of the apparatus, said container having means operative to create in the cannula a vacuum for drawing a cell sample into said cannula on activating the trigger, and means operatively associated with the trigger to prevent the vacuum from reaching the cannula when the trigger is released, said last-named means being also effective to deenergize the motor on termination of vacuum.

2. Apparatus according to claim 1, comprising means for regulating the stroke frequency of the cannula.

3. Apparatus according to claim 1, comprising means for regulating the stroke length of the cannula.

4. Apparatus according to claim 1, comprising a connecting hose between the cannula and the container.

5. Apparatus according to claim 1, wherein the motor comprises an electromagnet having a pivotable pole shoe which is connected to the cannula.

6. Apparatus according to claim 1, wherein the motor comprises a hydraulic motor.

7. Apparatus according to claim 1, comprising latching means arranged to prevent starting of the motor before a vacuum has been created in the cannula.

8. Apparatus according to claim 1, wherein the hand-grip comprises a casing in form of a holder for the apparatus components, and means are provided for providing a visual indication of the depth to which the cannula is inserted and thus the length of the stroke of the cannula.

9. Apparatus according to claim 1, wherein said means to create a vacuum in the cannula comprises a movable plunger within the container, said plunger having a shoulder and a flip-over means engaging said shoulder for locking the plunger in its moved position.

10. Apparatus according to claim 9, wherein first switch means is included proximate said flip-over means for actuation thereby should said plunger shoulder force the flip-over means upward, as may occur should the plunger be drawn upwardly by the force of the vacuum created.

11. Apparatus according to claim 10, wherein second switch means is provided which is in an operating circuit for said motor, said second switch means being operated by suction when applied to the cannula, said first switch means being in series connection with said second switch means in said motor operating circuit, said motor being deenergized on opening either or both of said first and second switch means.

* * * * *